United States Patent [19]

Nishihira et al.

[11] Patent Number: 5,705,677

[45] Date of Patent: Jan. 6, 1998

[54] DIPHENYL OXALATE-PHENOL ADDUCT, PROCESS FOR PRODUCING THE ADDUCT AND METHOD OF PRODUCING DIPHENYL OXALATE FROM THE ADDUCT

[75] Inventors: Keigo Nishihira; Shuji Tanaka; Yuki Nishida; Hirofumi Ii; Satoru Fujitsu, all of Ube, Japan

[73] Assignee: Ube Industries, Ltd., Ube, Japan

[21] Appl. No.: 757,070

[22] Filed: Nov. 26, 1996

[30] Foreign Application Priority Data

Nov. 28, 1995 [JP] Japan ................................ 7-309100
Nov. 28, 1995 [JP] Japan ................................ 7-309101

[51] Int. Cl.$^6$ .................................................. C07C 69/36
[52] U.S. Cl. ........................................................ 560/146
[58] Field of Search ............................................. 560/146

[56] References Cited

U.S. PATENT DOCUMENTS 5,239,106  8/1993  Shafer ................................ 558/274

OTHER PUBLICATIONS

Fritz Feigl und Riva Kobiliansky: Uber Vorverbindungen bei der Veresterung von Oxalsaure mit Phenolen, 1925, pp. 1483–1488, Berichte Der Chemisciien Gesellschaft.

*Primary Examiner*—Michael G. Ambrose
*Attorney, Agent, or Firm*—Burgess, Ryan & Wayne

[57] ABSTRACT

A novel crystalline adduct of diphenyl oxalate and phenol in a molar ratio of 1:2 and having a high purity is produced by melting a mixture containing diphenyl oxalate and phenol at a temperature of 100° C. or more; cooling the melt to a temperature of less than 100° C. to allow a resultant adduct of diphenyl oxalate and phenol in a molar ratio of 1:2 to crystallize and deposit from the melt; and collecting the crystalline adduct. Diphenyl oxalate with a high purity is produced by melting the crystalline adduct to dissociate it into diphenyl oxalate and phenol, and evaporating away the dissociated phenol from the melt to collect the dissociated diphenyl oxalate.

7 Claims, 1 Drawing Sheet

DIPHENYL OXALATE-PHENOL ADDUCT, PROCESS FOR PRODUCING THE ADDUCT AND METHOD OF PRODUCING DIPHENYL OXALATE FROM THE ADDUCT

BACKGROUND OF THE INVENTION

1. Field of the Invention

The present invention relates to a crystalline diphenyl oxalate-phenol adduct, a process for producing the adduct and a method of producing diphenyl oxalate from the adduct. More particularly, the present invention relates to a crystalline adduct of diphenyl oxalate and phenol in a molar ratio of 1:2, a process for producing the adduct from a melt of a mixture of diphenyl oxalate and phenol by applying a crystallization procedure thereto, and a method of producing diphenyl oxalate having a high degree of purity from the crystalline diphenyl oxalate-phenol adduct.

The crystalline adduct of diphenyl oxalate and phenol in a molar ratio of 1:2 is a novel substance and can be obtained in a high degree of purity. Also, the crystalline diphenyl oxalate-phenol adduct can be easily decomposed into diphenyl oxalate and phenol by heating the adduct, and thus is useful as an intermediate material for producing diphenyl oxalate in a high degree of purity.

The diphenyl oxalate produced by the method of the present invention is useful as an intermediate compound for producing various medicines, agricultural chemicals, polymers and additive for polymers.

2. Related Art

U.S. Pat. No. 5,239,106 to S. J. Shafer discloses a crystalline adduct of diphenyl carbonate and phenol. Nevertheless, it has not been known that diphenyl oxalate can addition-react with phenol to form a crystalline adduct thereof.

Also, diphenyl oxalate has not yet been produced in a large amount at an industrial scale, and it has not been known how to industrially produce diphenyl oxalate with a high degree of purity.

It is known that diphenyl oxalate with a high degree of purity can be produced, at a laboratory scale, by distilling a crude material containing diphenyl oxalate, for example, an ester-interchange reaction product containing diphenyl oxalate and phenol. If this laboratory distillation method is carried out at an industrial scale, since the distillation procedure must be carried out at a high temperature due to the high boiling temperature of diphenyl oxalate of 330° C., diphenyl oxalate and other compounds (for example, non-reacted starting compounds for the ester-interchange reaction) are deteriorated during the distillation so as to reduce the degree of purity and yield of the products.

Also, the distillation procedure for diphenyl oxalate having a high boiling temperature must be carried out under vacuum, and thus the distillation apparatus is complicated and requires a large amounts of energy to operate. Accordingly, the distillation method is unsatisfactory for industrial use.

SUMMARY OF THE INVENTION

An object of the present invention relates to provide a novel crystalline adduct of diphenyl oxalate and phenol, a process for producing the crystalline diphenyl oxalate-phenol adduct with a high degree of purity in a high yield, and a method of producing diphenyl oxalate with a high degree of purity from the crystalline adduct, which method can be carried out at an industrial large scale with high efficiency.

The novel substance of the present invention is a crystalline adduct of diphenyl oxalate and phenol in a molar ratio of 1:2.

The process of the present invention for producing a crystalline adduct of diphenyl oxalate and phenol comprises the steps of:

melting a mixture containing diphenyl oxalate and phenol at a temperature of 100° C. or more;

cooling the melt to a temperature of less than 100° C. to allow a resultant adduct of diphenyl oxalate and phenol in a molar ratio of 1:2 to crystallize and deposit from the melt; and collecting the resultant crystalline diphenyl oxalate-phenol adduct.

The method of the present invention for producing diphenyl oxalate from the above-mentioned crystalline diphenyl oxalate-phenol adduct comprises the steps of:

melting a crystalline diphenyl oxalate-phenol adduct having a molar ratio of 1:2 to dissociate the adduct into diphenyl oxalate and phenol; and evaporating away the dissociated phenol from the melt to collect the dissociated diphenyl oxalate.

DESCRIPTION OF THE PREFERRED EMBODIMENTS

Figure 1:
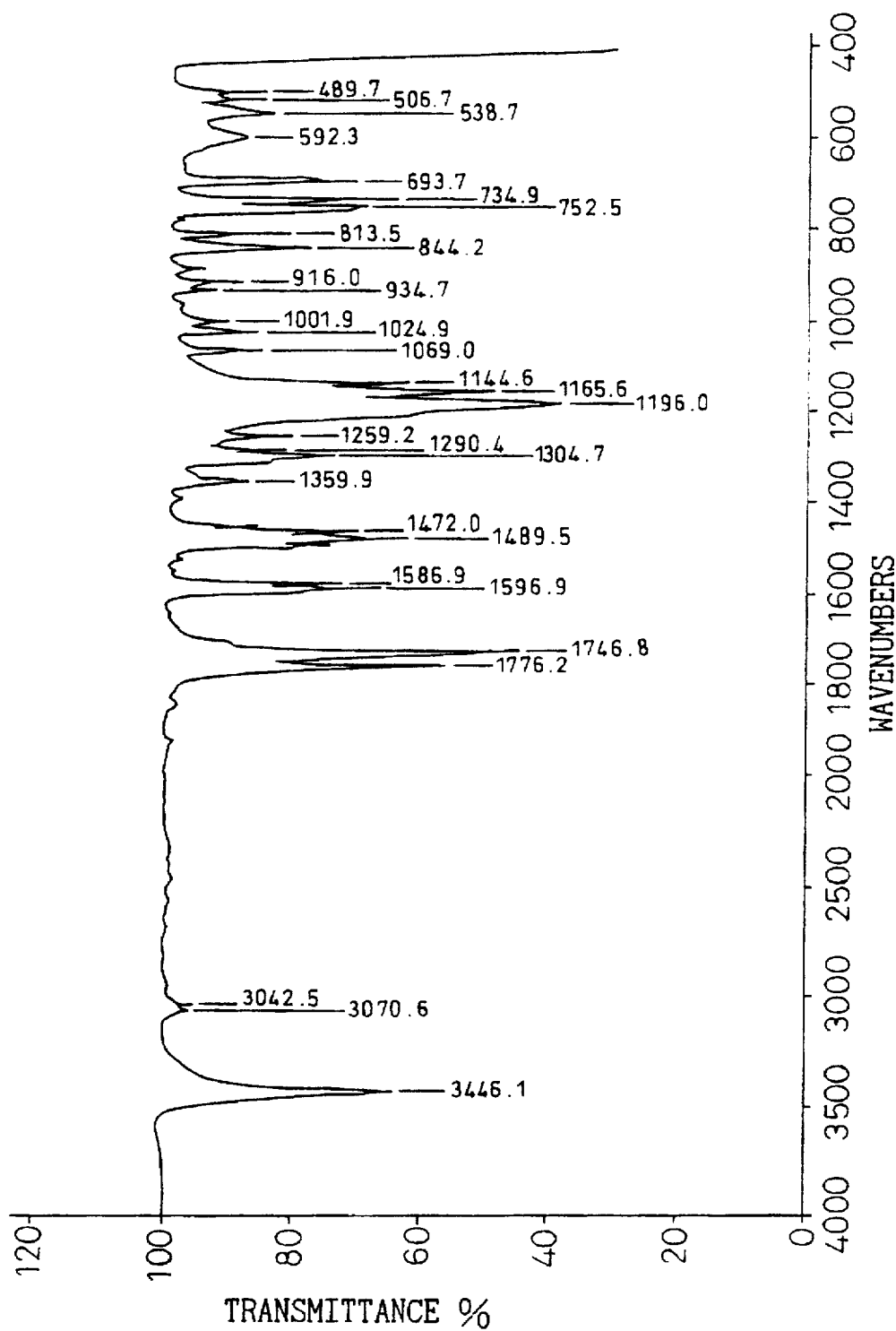
FIG. 1 shows a FT-IR spectrum of the diphenyl oxalate-phenol adduct of the present invention.

With respect to the novel crystalline adduct of diphenyl oxalate with phenol of the present invention, it has been confirmed by a gas chromatographic analysis that diphenyl oxalate and phenol are addition-reacted with each other in a molar ratio of 1:2, and the adduct is crystalline and has a formular weight of 430.64 and a melting temperature of 101° to 103° C.

Also, the diphenyl oxalate-phenol adduct of the present invention exhibits a FT-IR spectrum shown in FIG. 1.

Also, in a nuclear magnetic resonance spectrum ($^1$H-NMR) of the diphenyl oxalate-phenol adduct crystals, the peaks as shown in Table 1 appeared.

TABLE 1

| $\delta(CDCl_3)$ ppm | Classification |
| --- | --- |
| 4.85 | 2H, s |
| 6.82 | 4H, d |
| 6.92 | 2H, t |
| 7.23 | 8H, m |
| 7.32 | 2H, t |
| 7.46 | 4H, t |

The diphenyl oxalate-phenol adduct in a molar ratio of 1:2 can be produced by the process of the present invention which can be advantageously utilized for industrial practice.

In the process of the present invention, a mixture containing diphenyl oxalate and phenol is melted. In this melt, preferably, the content of diphenyl oxalate is in the range of from 1 to 50% by weight, more preferably 2 to 45% by weight, based on the total weight of diphenyl oxalate and phenol in the melt, and diphenyl oxalate and phenol are uniformly mixed in the state of a liquid. If the content of diphenyl oxalate is too high, it may be difficult to crystallize-deposit the resultant diphenyl oxalate-phenol adduct from the melt. Also, the melt preferably contains diphenol oxalate and phenol in a total content of 50% by weight, more preferably 60 to 100% by weight, still more preferably, 65 to 95% by weight, based on the total weight of the melt.

In the process of the present invention, the mixture to be melted may contain, in addition to diphenyl oxalate and phenol, foreign substances, for example, oxalic acid derivatives other than diphenyl oxalate, for example, dimethyl oxalate and methylphenyl oxalate, and phenyl derivatives other than phenol, for example, carboxylic acid phenyl esters and diphenyl carbonate, which substances do not deposit from the melt under the conditions suitable for crystallize-depositing the diphenyl oxalate-phenol adduct of the present invention, are compatible with diphenyl oxalate and phenol and have a melting temperature of lower than 150° C., preferably lower than 100° C. The foreign substances are present preferably in a total content of less than about 50% by weight, more preferably 0 to 40% by weight, still more preferably 0 to 30% by weight, based on the total weight of the mixture.

The mixture containing diphenyl oxalate and phenol may be a reaction product mixture obtained from various diphenyl oxalate-producing processes and containing diphenyl oxalate and phenol or an admixture of the above-mentioned reaction product mixture with an additional amount of phenol having a composition adjusted as mentioned above. Alternatively, the diphenyl oxalate and phenol-containing mixture can be prepared by mixing a diphenyl oxalate mixture having a diphenyl oxalate content of 80 to 100% by weight with a phenol mixture having a phenol content of 80 to 100% by weight, in a desired weight mixing ratio.

The mixture containing diphenyl oxalate and phenol is melted at a temperature of 100° C. or more, preferably 120° C. to 300° C., still more preferably 140° C. to 250° C. to provide a uniform melt.

In an example, the melt of the mixture containing diphenyl oxalate and phenol is prepared by ester-interchange reacting dialkyl oxalate with phenol or a phenol derivative, for example, a carboxylic acid phenyl ester or diphenyl carbonate at a temperature of 100° C. or more. The resultant reaction product mixture in the state of a melt can be utilized as a melt of the mixture containing diphenyl oxalate and phenol for the industrial practice. Also, the reaction product mixture melt may be mixed with an additional amount of phenol to control the composition of the melt.

Especially, in the industrial production of the diphenyl oxalate-phenol adduct, the reaction product mixture in the state of a melt prepared by the ester-interchange reaction of a dialkyl oxalate with phenol at a temperature of 100° C. or more is preferably utilized as a melt of the mixture containing diphenyl oxalate and phenol.

In the production of the crystalline diphenyl oxalate-phenol adduct of the present invention, even when the above-mentioned reaction product mixture melt containing a catalyst for the ester-interchange reaction is used as a diphenyl oxalate and phenol-containing mixture melt, the resultant adduct crystals deposited from the melt are substantially free from the catalyst and thus have a high degree of the purity. Namely, the process of the present invention is advantageous in that the diphenyl oxalate-phenol adduct crystals having a high degree of purity can be easily obtained without using a complicated refining procedure.

In the process of the present invention, a uniform mixture containing diphenyl oxalate and phenol is melted at a temperature of 100° C. or more, the resultant uniform mixture melt is cooled to a temperature of less than 100° C., preferably 10° to 95° C. to allow a resultant adduct of diphenyl oxalate and phenol in a molar ratio of 1:2 to crystallize and deposit from the melt. The deposited adduct crystals are collected from the melt by a conventional crystal-collecting procedure, for example, a filtration or centrifugal procedure.

The crystallization procedures can be carried out by gradually and continuously decreasing the temperature of the melt. If necessary, a combination of a crystallization procedure with an adduct crystal-collection procedure can be repeated two or three or more times at different crystallization temperatures, to enhance the collection yield of the adduct crystals.

In the process of the present invention, the crystallize-deposition procedure can be carried out in a conventional apparatus, for example, a conventional deposition vessel equipped with a conventional stirrer.

The crystallization procedure is preferably carried out in a temperature range in which a matrix portion of the melt other than the resultant adduct crystals is maintained at the state of a melt. For example, when the adduct crystals are deposited from the melt matrix containing 50% by weight or more of phenol, the crystallization and collection procedures are preferably carried out at a temperature of 40° C. or more, more preferably 45° to 90° C., still more preferably 50° to 80° C.

In the case where the reaction product mixture obtained by the process for producing diphenyl oxalate by the ester-interchange reaction of dialkyl oxalate with a phenol compound is used as a diphenyl oxalate and phenol-containing mixture, and the resultant adduct crystals are collected from the melt of the reaction product mixture by a filtration or centrifugal separation, the collection residue contains non-reacted dialkyl oxalate, alkylphenyl oxalate, diphenyl oxalate and phenol. Therefore, the collection residue can be recycled to and reused in the diphenyl oxalate-producing process.

Since the diphenyl oxalate-phenol adduct crystals of the present invention produced by the process of the present invention have a high degree of purity and can be easily dissociated into diphenyl oxalate and phenol by heating the adduct crystals at a temperature higher than the melting temperature thereof. Accordingly, in the method of the present invention, diphenyl oxalate with a high degree of purity can be produced by melting the crystalline diphenyl oxalate-phenol adduct in a molar ratio of 1:2, to dissociate the adduct into diphenyl oxalate and phenol; and evaporating away the dissociated phenol from the melt to collect the dissociated diphenyl oxalate.

In the method of the present invention, the melting procedure is carried out at a temperature equal to or higher than the melting temperature of the adduct, namely 101° to 103° C. or more, preferably 136° C. or more. However, the melting temperature is preferably not higher than 300° C., more preferably not higher than 250° C., and still more preferably not higher than 220° C., to prevent thermal deterioration of diphenyl oxalate.

Also, the evaporation procedure for removing the dissociated phenol from the melt, which procedure may be a distillation procedure, is preferably carried out while maintaining the temperature of the melt at 300° C. or less, more preferably 250° C. or less, and still more preferably 220° C. or less under the ambient atmospheric pressure or a reduced pressure. The removal of phenol by the evaporation or distillation procedure may be carried out simultaneously with the melting procedure of the adduct.

In the method of the present invention, to obtain diphenyl oxalate with a high degree of purity, the evaporation or distillation procedure for the removal of phenol is preferably carried out while continuously maintaining the adduct at the state of a melt. Since the melting temperature of diphenyl oxalate is 136° C., the temperature of the adduct melt is preferably maintained at 136° C. or more, more preferably 140° C. or more, and still more preferably 145° C. or more from the initial stage at which the concentration of the dissociated diphenyl phenol in the melt gradually increases to the final stage at which the dissociation of the diphenyl oxalate-phenol adduct is substantially completed.

Accordingly, in the method of the present invention, the adduct melt is heated and maintained preferably at a temperature of 100° to 300° C., more preferably 140° to 250° C., and still more preferably 145° to 220° C. throughout the evaporation procedure, to evaporate away the dissociated phenol and collect the dissociated diphenyl oxalate having a high degree of purity, usually about 100%.

In the melting procedure, the temperature of the melt may be gradually increased with an increase in the concentration of the dissociated diphenyl oxalate in the melt. For example, the evaporation procedure may be carried out in multiple steps, for example, at a temperature of 100° to 140° C. in the initial step and at a temperature of 140° to 250° C. in the final step.

To evaporate away the dissociated phenol at a high efficiency, the melt is preferably heated to and maintained at a temperature equal to or higher than the boiling temperature of phenol, namely 182° C., more preferably 190° C. or more.

Namely, the evaporation or distillation procedure in the method of the present invention is carried out preferably in the temperature range of from 182° C. to 300° C., more preferably from 190° to 250° C., still more preferably from 190° to 220° C.

Also, in the method of the present invention, to reduce the thermal deterioration of the dissociated diphenyl oxalate and phenol, the melting and evaporation temperatures are preferably maintained within the range of from 100° to 300° C. under a reduced pressure of 270 to 67,000 Pa (2 to 500 mHg).

The resultant diphenyl oxalate by the method of the present invention has a high degree of purity of 95% by weight or more, usually 97 to 100% by weight, and thus is useful for various uses as mentioned above.

EXAMPLES

The present invention will be further explained by the following examples.

Example 1

A mixture of 100.26 g (0.413 mole) of diphenyl oxalate (made by Wako Junyaku K. K.) with 450.0 g (4.80 moles) of phenol (made by Wako Junyaku K. K.) was placed in a 500 ml glass round flask equipped with a thermometer and a stirrer and arranged on a heating oil bath. The heating of the mixture by the oil bath was started while stirring the mixture. After heating at a temperature of 150° C. for 30 minutes, a uniform melt of the mixture of diphenyl oxalate with phenol was obtained. Then the heating was stopped and the mixture melt was gradually cooled. When the mixture melt temperature reached 81° C., deposition of crystals was started. The mixture melt was stirred at this temperature for 30 minutes, and the deposited crystals were collected by filtration. The resultant crystals were dried at a temperature of 60° C. under vacuum for 5 hours. The collected crystals were subjected to the following measurement and analysis.

Measurement of Melting Point

The crystals exhibited a melting point of 101° to 103° C. which is different from the melting points of either diphenyl oxalate or phenol.

Gas Chromatographic Analysis

The crystals were dissolved in acetonitrile and subjected to gas chromatographic analysis. As a result, diphenyl oxalate and phenol were detected in addition to acetonitrile, and the detected diphenyl oxalate and phenol were found in amounts corresponding to a weight ratio of 1:0.78 and a molar ratio of diphenyl oxalate to phenol of 1:2.

GC-MS Analysis

The crystals were subjected to GC-MS analysis. As a result, diphenyl oxalate having a molecular weight of 242 and phenol having a molecular weight of 94 were confirmed.

Elemental Analysis

The crystals were subjected to elemental analysis. The analytical results shown in Table 2 corresponded to an adduct of diphenyl oxalate and phenol in a molar ratio of 1:2.

TABLE 2

| Element | Analytical value (% by weight) | Theoretical value (% by weight) |
|---|---|---|
| C | 71.98 | 72.55 |
| H | 5.23 | 5.12 |
| O | 22.78 | 22.33 |

FT-IR Analysis

The crystals exhibited a FT-IR spectrum shown in FIG. 1.

$^1$H-NMR Analysis

The crystals were subjected to $^1$H-NMR analysis. The resultant $^1$H-NMR spectrum exhibited the following peaks.

| δ(CDCl$_3$) ppm | |
|---|---|
| 4.85 | (2H, s) |
| 6.82 | (4H, d) |
| 6.92 | (2H, t) |
| 7.23 | (8H, m) |
| 7.32 | (2H, t) |
| 7.46 | (4H, t) |

From the above-mentioned analytical results, it was confirmed that the crystals consist of a novel adduct of diphenyl oxalate and phenol in a molar ratio of 1:2.

Example 2

A mixture containing diphenyl oxalate and phenol in the state of a melt was prepared by the following procedures.

A round glass flask having a capacity of 1000 ml and equipped with a thermometer and a stirrer was charged with a mixture of 118.0 g (1.00 mole) of dimethyl oxalate (made by Wako Junyaku K. K.) with 470.2 g (5.00 moles) of phenol (made by Wako Junyaku K. K.) and 1.01 g (0.0024 mole) of tetraphenoxytitanium and placed on a heating oil bath. The mixture in the flask was heated by the oil bath to a temperature of 180° C. to 200° C. and maintained at this temperature for 8 hours, while stirring the mixture and distilling away the generated methyl alcohol due to an ester-interchange reaction of dimethyl oxalate with phenol.

After completion of the reaction, a portion of the resultant reaction product mixture was subjected to gas chromatographic analysis. It was confirmed that the reaction product mixture contained 21.38% by weight of diphenyl oxalate, 12.47% by weight of methylphenyl oxalate, 3.86% by weight of dimethyl oxalate and 62.05% by weight of phenol.

The reaction product mixture in the state of a melt and containing diphenyl oxalate and phenol uniformly mixed with each other was stopped to be heated and gradually cooled from the temperature of 180° to 200° C. When the temperature of the melt reached about 85° C., it was found that deposition of crystals started. The temperature of the melt was further decreased to 60° C. to continue the deposition of the crystals. The deposited crystals were collected at the temperature of 60° C. by filtration, rinsed with about 50 ml of phenol and dried at a temperature of 60° C. for 5 hours under a reduced pressure. The filtrate contained 3.05% by weight of diphenyl oxalate, 18.42% by weight of methylphenyl oxalate, 5.72% by weight of dimethyl oxalate and 72.80% by weight of phenol.

The resultant crystals were subjected to the same measurement and analysis as in Examples 1. It was confirmed by the measurement and analysis results that the resultant crystals consisted of a diphenyl oxalate-phenol adduct in a molar ratio of 1:2.

Example 3

The same diphenyl oxalate-phenol adduct as in Example 2 in an amount of 150 g and in the wetted condition was placed in a single distillation apparatus and heat-melted at a temperature of 110° to 120° C. under a reduced pressure of 2700 Pa (20 mmHg), and the dissociated phenol was distilled away from the melt. The distillation residue in an amount 74.3 g consisted essentially of diphenyl oxalate having a degree of purity of 99% or more determined by gas chromatography.

In the present invention, a new adduct of diphenyl oxalate and phenol in a molar ratio of 1:2 can be produced in a high degree of purity by a simple and easy process and apparatus, and can be utilized to produce diphenyl oxalate with a high degree of purity by a simple and easy method and apparatus.

We claim:

1. A process for producing a crystalline adduct of diphenyl oxalate and phenol, comprising the steps of:
   melting a mixture containing diphenyl oxalate and phenol at a temperature of 100° C. or more,
   cooling the melt to a temperature of less than 100° C. to allow a resultant adduct of diphenyl oxalate and phenol in molar ratio of 1:2 to crystallize and deposit from the melt; and
   collecting the resultant crystallized diphenyl oxalate-phenol adduct.

2. The process as claimed in claim 1, wherein the melt prepared in the melting step contains diphenyl oxalate in a content of 1 to 50% by weight based on the total weight of diphenyl oxalate and phenol.

3. The process as claimed in claim 1, wherein the cooling is carried out at a temperature of 10° C. to 95° C.

4. A method of producing diphenyl oxalate from the crystalline diphenyl oxalate-phenol adduct as claimed in claim 1, comprising the steps of:
   melting a crystalline diphenyl oxalate-phenol adduct having a molar ratio of 1:2 to dissociate the adduct into diphenyl oxalate and phenol; and
   evaporating away the dissociated phenol from the melt to collect the dissociated diphenyl oxalate.

5. The method as claimed in claim 4, wherein the phenol-evaporation is carried out at a temperature of 100° C. to 300° C.

6. The method as claimed in claim 5, wherein the phenol-evaporation temperature is from 190° C. to 250° C.

7. The method as claimed in claim 4, wherein the phenol-evaporation is carried out under a reduced pressure of from 270 to 67,000 Pa.

* * * * *